US008664283B2

(12) United States Patent
Blanchard et al.

(10) Patent No.: US 8,664,283 B2
(45) Date of Patent: Mar. 4, 2014

(54) PURIFICATION OF ACETIC ACID PRODUCT STREAMS

(75) Inventors: Greg Blanchard, Manvel, TX (US); Ronald D. Shaver, Houston, TX (US); Brian W. Hokkanen, Houston, TX (US); G. Paull Torrence, League City, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 13/338,612

(22) Filed: Dec. 28, 2011

(65) Prior Publication Data

US 2012/0202900 A1 Aug. 9, 2012

Related U.S. Application Data

(60) Provisional application No. 61/428,464, filed on Dec. 30, 2010.

(51) Int. Cl.
*C07C 51/47* (2006.01)

(52) U.S. Cl.
USPC .......... 521/31; 502/60; 502/64; 562/608

(58) Field of Classification Search
USPC .................. 521/31; 502/60, 64; 562/608
See application file for complete search history.

(56) References Cited

U.S. PATENT DOCUMENTS

| 3,769,329 | A | 10/1973 | Paulik et al. |
| 4,615,806 | A | 10/1986 | Hilton |
| 4,994,608 | A | 2/1991 | Torrence et al. |
| 5,001,259 | A | 3/1991 | Smith et al. |
| 5,026,908 | A | 6/1991 | Smith et al. |
| 5,139,981 | A | 8/1992 | Kurland |
| 5,144,068 | A | 9/1992 | Smith et al. |
| 5,227,524 | A | 7/1993 | Jones |
| 5,653,853 | A | 8/1997 | Kagotani et al. |
| 5,672,743 | A | 9/1997 | Garland et al. |
| 5,731,252 | A | 3/1998 | Warner et al. |
| 5,840,969 | A | 11/1998 | Joensen |
| 5,917,089 | A | 6/1999 | Howard |
| 5,962,735 | A | 10/1999 | Kulprathipanja et al. |
| 6,225,498 | B1 * | 5/2001 | Blay et al. ............... 562/608 |
| 6,339,171 | B1 | 1/2002 | Singh et al. |
| 6,642,168 | B1 * | 11/2003 | Latus ........................... 502/64 |
| 6,657,078 | B2 | 12/2003 | Scates et al. |
| 7,005,541 | B2 | 2/2006 | Cheung et al. |
| 7,202,382 | B2 | 4/2007 | Muskett |
| 7,223,886 | B2 | 5/2007 | Scates et al. |
| 2008/0287706 | A1 | 11/2008 | Powell et al. |
| 2008/0293966 | A1 | 11/2008 | Scates et al. |
| 2009/0107833 | A1 | 4/2009 | Warner |
| 2009/0270651 | A1 | 10/2009 | Zinobile et al. |

FOREIGN PATENT DOCUMENTS

| CN | 101209428 A | | 7/2008 |
| EP | 0482787 A2 | | 4/1992 |
| JP | 09-291058 | * | 11/1997 |
| JP | 9291058 A | | 11/1997 |
| WO | 0056454 A1 | | 9/2000 |
| WO | 02062740 A1 | | 8/2002 |

OTHER PUBLICATIONS

International Search Report and Written Opinion for PCT/US2011/067564, mailed Mar. 30, 2012.
U.S. Appl. No. 12/892,348, filed Sep. 28, 2010, Torrence, et al.
J. H. Jones (2002), "The Cativa™ Process for the Manufacture of Acetic Acid", Platinum Metals Review, 44(3): 94-105.
International Written Opinion mailed Dec. 14, 2012 in corresponding International Application No. PCT/US2011/067564.
International Preliminary Report on Patentability mailed Apr. 26, 2013 in corresponding International Application No. PCT/US2011/067564.

* cited by examiner

*Primary Examiner* — Peter D. Mulcahy
*Assistant Examiner* — Henry Hu

(57) ABSTRACT

In one embodiment, the invention is to an ion exchange resin composition comprising a metal-functionalized exchange resin comprising from 3% to 94% metal-functionalized active sites; and a non-metal-functionalized exchange resin comprising non-metal-functionalized active sites.

19 Claims, No Drawings

PURIFICATION OF ACETIC ACID PRODUCT STREAMS

CROSS REFERENCE TO RELATED APPLICATION

This application claims priority to U.S. Provisional patent application No. 61/428,464, which was filed on Dec. 30, 2010. The entirety of this application is incorporated by reference herein.

FIELD OF THE INVENTION

This invention relates generally to the removal of iodides from a crude acetic acid product and, in particular, to an ion exchange resin composition, optionally for use in an iodide guard bed, to facilitate removal of iodides.

BACKGROUND OF THE INVENTION

Commercial processes for the production of acetic acid are known. Several conventional processes involve the catalyzed carbonylation of methanol with carbon monoxide. Examples of these conventional processes include those described in U.S. Pat. Nos. 3,769,329, 5,001,259, 5,026,908, and 5,144,068, which are hereby incorporated by reference.

One of the most widely used processes for the manufacture of acetic acid is the Monsanto process, which involves carbonylating methanol in the presence of rhodium, methyl iodide, methyl acetate and water. The product is suitable for many conventional purposes. The acetic acid produced via the Monsanto process, however, suffers from iodide contamination. Another conventional methanol carbonylation process is the Cativa™ process, which is discussed in Jones, J. H. (2002), "*The Cativa™ Process for the Manufacture of Acetic Acid*," Platinum Metals Review, 44 (3): 94-105. Although fewer iodides often may be present due to the use of catalyst promoters, iodide contamination is still an issue with the crude acetic acid products of the Cativa™ Process.

Macroreticulated strong acid cationic exchange resin compositions are conventionally utilized to reduce iodide contamination. Suitable exchange resin compositions, e.g., the individual pellets thereof, comprise both sites that are functionalized with a metal, e.g., silver or palladium, and sites that are non-functionalized. Exchange resin compositions that have little or no metal-functionality do not efficiently remove iodides and, as such, are not conventionally used to do so. Typically, metal-functionalized exchange resins are provided in a guard bed and a stream comprising the crude acetic acid product is passed through the guard bed. In the guard bed, the iodide contaminants contained in the crude acetic acid product attach to these metal-functionalized sites and are removed from the acetic acid product stream. The non-metal-functionalized sites generally do not capture iodides.

The metal-functionalization of exchange resin compositions often involves significant processing and expense, often costing orders of magnitude more than resins that are not metal-functionalized. Often the process steps associated with the functionalization varies very little with regard to the actual amount of metal that is deposited on the exchange resin. For example, the processing necessary to functionalize 50% of the active sites of a quantity of exchange resin is quite similar to the processing necessary to functionalize 10% of the active sites of the same quantity of exchange resin. Because the entire quantity of exchange resin requires processing, however, both the 50%-functionalized exchange resin and the 10%-functionalized resin require significantly more processing than the same quantity of non-functionalized resin.

In addition to iodide contaminants, metals from the walls of the vessels used in the acetic acid production system often corrode and dissolve into the crude acetic acid product compositions. Thus, conventional acetic acid product streams often comprise corrosion metal contaminants as well as iodide contaminants. These corrosion metals are known to interfere with the carbonylation reaction or accelerate competing reactions such as the water-gas shift reaction. Typically, these corrosion metals may be removed from the process streams by passing the streams through resin guard beds comprising standard, non-metal-functionalized cationic exchange resins. It is not necessary nor economically practical to use an expensive metal-functionalized exchange resin to remove corrosion metals.

In a case where an exchange resin with individual pellets each comprising both functionalized and non-functionalized sites is utilized, however, the corrosion metals may detrimentally clog the metal-functionalized sites of the exchange resins. As such, the clogged sites are unable to capture/remove the iodide contaminants. As such, the lifetime of the functionalized resin, with regard to iodide removal, is shortened by the presence of corrosion metals. Often a pre-determined portion of the sites on each of the pellets of the exchange resin composition are functionalized, thus leaving the remainder of the sites available for corrosion metal removal. As a result, the non-functionalized active sites attract the corrosion metals while the functionalized sites remain available for iodide removal. Although this technique may improve the lifetime of exchange resins, the partial functionalization of the pre-determined portion of sites on each pellet requires significant processing and resources.

Thus, the need exists for a process for preparing an exchange resin composition comprising a predetermined portion of functionalized sites wherein the quantity of metal functionalized resin pellets in the exchange resin composition is reduced. By reducing the quantity of metal functionalized exchange resin pellets in the exchange resin composition, the overall processing required to prepare the exchange resin composition may be lessened.

SUMMARY OF THE INVENTION

The present invention, in one embodiment, is to a process for purifying a crude acetic acid composition. The crude acetic acid composition may comprise acetic acid, iodides, and corrosion metals. The process comprises the step of contacting the crude acetic acid composition with an ion exchange resin composition to form a purified acetic acid product. For example, the contacting of the crude acetic acid composition with an ion exchange resin composition may be conducted in a guard bed. As a result, at least 25 wt. % of the iodides and at least 25 wt. % of the corrosion metals in the crude acetic acid product may be removed from the crude acetic acid product. Further, the resulting purified acetic acid product may comprise less than 100 wppb iodides and less than 1,000 wppb corrosion metals.

In another embodiment, the invention is to an ion exchange resin composition comprising a metal-functionalized exchange resin comprising from 3% to 94% metal-functionalized active sites and a non-metal-functionalized exchange resin comprising non-metal-functionalized active sites. Preferably, the metal-functionalized exchange resin is functionalized with silver. In a preferred embodiment, the amount of metal-functionalized exchange resin and non-metal-functionalized exchange resin corresponds to the iodide content and the corrosion metal content, respectively, of the crude acetic acid composition. For example, the ratio of metal-functionalized active sites to non-metal-functionalized active sites may correspond to a molar ratio of iodides to corrosion metals in the crude acetic acid composition within a margin of error of ±25%, e.g. ±20% or ±10%.

DETAILED DESCRIPTION OF THE INVENTION

Introduction

Conventional crude acetic acid product compositions comprise both iodide contaminants and corrosion metal contaminants. Typically, these contaminants are removed by ion exchange resin compositions that comprise individual particles, e.g., pellets, that comprise both metal-functionalized and non-metal functionalized active sites. These conventional ion exchange resin compositions are produced via metal-functionalization processing of an entire quantity of resin composition. It has now been discovered that an ion exchange resin composition having both metal-functionalized active sites and non-metal functionalized active sites may be produced without metal-functionalizing the entire quantity of resin composition. For example, some pellets of the ion exchange resin may comprise no metal-functionalization, while other pellets are metal-functionalized in some amount.

The inventive ion exchange resins comprise a metal-functionalized exchange resin component and a non-metal-functionalized exchange resin component. The metal-functionalized exchange resin, e.g., the individual pellets thereof, comprises metal-functionalized sites. Preferably, from 3% to 94% of the active sites of the metal-functionalized exchange resin are functionalized. As used herein, a "non-metal-functionalized exchange resin," e.g., the individual pellets thereof, has not been metal-functionalized and does not contain any metal-functionalized active sites. Thus, a significant portion of the inventive ion exchange resin composition, e.g., the non-metal-functionalized exchange resin component, does not require metal-functionalization to any degree. Accordingly, the overall processing of the entire quantity of the inventive ion exchange resin composition, e.g., the metal-functionalized component and the non-metal-functionalized component, is significantly reduced.

The present invention also is to a process for purifying a crude acetic acid product composition comprising acetic acid, iodides, and corrosion metals. The process comprises the step of contacting the crude acetic acid product with the inventive ion exchange resin composition. In one embodiment, the amount of metal-functionalized exchange resin in the ion exchange resin composition corresponds, within a margin of error, to the iodide content in the crude acetic acid product and/or the amount of non-metal-functionalized exchange resin in the ion exchange resin composition corresponds to the corrosion metal content in the crude acetic acid product. Preferably, the amounts of metal-functionalized exchange resin and non-metal-functionalized exchange resin may be adjusted, e.g., tailored, to correspond to a particular crude acetic acid product. For example, the ratio of metal-functionalized sites to non-metal-functionalized sites in the ion exchange resin composition may correspond to the molar ratio of iodides to corrosion metals in the crude acetic acid product within a margin of error of ±25%, e.g. ±20% or ±10%.

Ion Exchange Resin Composition

As indicated above, the inventive ion exchange resin compositions comprise a metal-functionalized exchange resin component and a non-metal-functionalized exchange resin component. The metal-functionalized resin is produced by metal-functionalizing a base exchange resin, as discussed below. Thus, in one embodiment, the metal-functionalized exchange resin comprises a base resin and a functionalizing metal. The base exchange resin itself is not metal-functionalized, e.g., the base exchange resin does not comprise active sites that are metal-functionalized. The non-metal-functionalized exchange resin also is not metal-functionalized and may comprise a base resin. Thus, in some embodiments, the non-metal-functionalized exchange resin may be the same as the base resin used to prepare the metal-functionalized exchange resin. In other embodiments, the non-metal-functionalized exchange resin may different from the base exchange resin.

The exchange resins suitable for the inventive ion exchange resin compositions may be of the gel or macroreticular type. Preferably the base exchange resin and/or the non-metal-functionalized exchange resin are a macroreticular ion exchange resin. Examples of these resins are those of the $RSO_3$ H "strong acid" type, which are cation exchange resins of the macroreticular type. Macroreticular resins generally have a uniform pore structure and are distinguished from gel resins by their physical form. Specifically, macroreticular resin particles are comprised of agglomerated microspheres of gel resin fused into a particle having a net-like structure. This structure exhibits macropores within the agglomerated particle. Although the gel microspheres may shrink in carboxylic acid, this shrinkage does not affect the macroporous nature of the macroreticular particle. The macroreticular structure allows molecules having diameters larger than the interstices in a gel structure to come into contact with active sites located on the surface of a pore within the resin particle. Further, the macropores of the macroreticular resins do not depend on the ability of reactants to cause the resin structure to swell in order to afford access to the active sites via the macropores. With a macroreticular resin, molecules that do not swell the gel can move through the macropores to catalytically-active sites within the particle. In some embodiments, the diameter of the pores is controlled to achieve a particular macroporous structure. In one embodiment, for example, the average pore diameter of the macroreticular resins is above 25 microns, e.g., above 50 microns or above 75 microns.

The base resin used in the preparation of the metal-functionalized exchange resin may vary widely. In some embodiments, the base resin is selected from the group consisting of polystyrene, styrene/divinyl benzene polymer, polyvinyl pyrrolidone, polyvinyl pyridine, and macroreticulated strong acid cation exchange resins, with styrene/divinyl benzene polymer being preferred. Suitable commercial products include the Amberlyst™ series of macroreticular cation exchange resins from the Rohm and Haas subsidiary of Dow Chemical Company, with Amberlyst™ 15 being preferred. Other stable ion exchange resins such as zeolites may be employed, provided that the material is stable in the organic medium at the conditions of interest, e.g., the resins will not chemically decompose or release metal into the organic medium in unacceptable amounts. Zeolite cationic ion exchange substrates are disclosed, for example, in U.S. Pat. No. 5,962,735, which is hereby incorporated by reference in its entirety.

Cation-exchange forms of such resins typically comprise sulfonic acid groups, which may act as the active sites. In one embodiment, monovalent cations bond to the sulfonic acid groups and become part of the active sites. Any monovalent cation, for example $Na^+$ or $H^+$, may be used with the sulfonic groups to form the active sites, with H⁺ being preferred. In cases where the exchange resin is to be metal-functionalized on the sulfonic acid groups, the monovalent metal cation is preferably selected such that the resin has less affinity for the monovalent cation than for the metal used in the functionalization. Typically, exchange resins comprise individual, discrete particles, e.g., pellets, and the active sites are distributed over at least a portion of the surface of each particle. In some embodiments, the exchange resins have a preponderance of active sites, and the active sites may be distributed throughout the particles of the resin. Thus, each of the pellets of exchange resin, e.g., base exchange resin, comprises active sites, and these active sites may be or may not be subsequently functionalized with a selected metal, e.g., silver or palladium. The number of active sites per unit mass or per unit volume of resin may vary over a wide range. The quantity of active sites available on a resin is reflected in the molar capacity of a particular resin, which is expressed as milliequivalents per gram (mEq/g). In one embodiment, the molar capacity of the exchange resin ranges from 0.2 mEq/g to 10 mEq/g, e.g., from 0.5 mEq/g to 6 mEq/g.

In the present invention, each of the pellets of the metal-functionalized exchange resin component comprises a portion of active sites that have been functionalized, e.g., with silver or palladium. Each individual pellet of the non-metal-functionalized exchange resin, in contrast, does not contain any active sites that have been metal-functionalized. Thus, the non-metal-functionalized exchange resin component beneficially does not require a functionalization step with the selected metal, e.g., silver or palladium. In contrast, conventional guard bed resins comprise pellets each of which comprise both metal-functionalized active sites and non-metal-functionalized sites. Each pellet of conventional guard bed resins has some degree of metal-functionalization and requires a metal-functionalization step.

The combination of metal-functionalized exchange resin and non-metal-functionalized exchange resin, according to the invention, provides an inventive ion exchange resin composition, which comprises a predetermined number of metal-functionalized active sites and a predetermined number of non-metal-functionalized active sites. Unlike conventional exchange resins, however, only a portion of the inventive ion exchange resin composition, e.g., the metal-functionalized exchange resin component, is subjected to the metal-functionalization process.

In one embodiment, the ion exchange resin composition comprises at least 3% metal-functionalized active sites, e.g., at least 5%, at least 6%, at least 10%, at least 25%, or at least 50%. In terms of upper limits, the ion exchange resin composition may comprise less than 90% metal-functionalized active sites, e.g., less than 70%, less than 50%, less than 25%, or less than 10%. In other embodiments, the ion exchange resin comprises at least 3% non-metal-functionalized sites, e.g., at least 5%, at least 6%, at least 10%, at least 25%, at least 50% at least 70%, or at least 90%. In terms of upper limits, the ion exchange resin composition may comprise less than 90% non-metal-functionalized active sites, e.g., less than 70%, less than 50%, less than 25%, or less than 10%. It will be appreciated that some amount of metal-functionalized sites and some amount of non-metal-functionalized sites should be present in the ion exchange resins of the present invention. Some exemplary ion exchange resin compositions are provided in Table 1.

TABLE 1

Exemplary Ion Exchange Resin Active Site Compositions

| | % | % | % |
|---|---|---|---|
| Metal-Functionalized Active Sites | 3 to 94 | 10 to 90 | 25 to 75 |
| Non-Metal Functionalized Active Sites | 6 to 97 | 10 to 90 | 25 to 75 |

In some embodiments, the amounts of metal-functionalized active sites and non-metal-functionalized active sites may correspond (within a margin of error, e.g., ±25%, ±20% or ±10%) to the amounts of iodides and corrosion metals in a particular crude acetic acid product, respectively. In one embodiment, based on the amounts of iodides and corrosion metals, the ion exchange catalyst may be prepared to have the appropriate ratio, e.g., molar ratio, of metal-functionalized active sites to non-metal-functionalized active sites. In one embodiment, in a crude acetic acid product, corrosion metal content may range from 10 wppb to 2000 wppb, e.g., 25 wppb to 1500 wppb and iodide content may range from 50 wppb to 2000 wppb, e.g., from 100 wppb to 1000 wppb. Preferably, the ratio of non-metal-functionalized active sites to metal-functionalized active sites in the inventive ion exchange resin composition ranges from 17:1 to 0.02:1, e.g., from 15:1 to 0.1:1, or from 10:1 to 0.1:1. As one example, if the molar ratio of iodides to corrosion metals in the crude acetic acid product is 2:1, then the molar ratio of metal-functionalized active sites to non-metal-functionalized active sites may be 2:1 (±25%). Examples of other metal-functionalized to non-metal-functionalized site ratios include, but are not limited to 1:1 and 3:1.

As indicated above, the metal-functionalized active sites remove iodide contaminants, while the non-metal-functionalized active sites remove corrosion metal contaminants. As such, a particular resin composition may be tailored to remove iodide and corrosion metals from a crude acetic acid product having a known composition of these contaminants. As one example of this tailoring, the amounts of the metal-functionalized exchange resin and the non-metal-functionalized exchange resin may be varied to yield a desired metal-functionalized to non-metal-functionalized site ratio as discussed above. In doing so, the non-metal-functionalized active sites remove the corrosion metal impurities while the metal-functionalized active sites remain available for iodide removal. In doing so, the overall lifetime of the ion exchange resin composition is advantageously improved.

The metal-functionalized active sites and non-metal-functionalized active sites are, in one embodiment, provided by the respective ion exchange resin component. In one embodiment, the ion exchange resin composition comprises at least 1 wt % metal-functionalized exchange resin, e.g., at least 10 wt %, at least 25 wt %, at least 50 wt %, at least 75 wt %, or at least 90 wt %. In terms of upper limits, the ion exchange resin composition may comprise less than 99 wt % metal-functionalized exchange resin, e.g., less than 90 wt %, less than 70 wt %, less than 50 wt %, less than 25 wt %, less than 10 wt %, or less than 1 wt %, while appreciating that some amount of metal-functionalized exchange resin should be present in the ion exchange resin composition. In other embodiments, the ion exchange resin composition comprises at least 1 wt % non-metal-functionalized exchange resin, e.g., at least 10 wt %, at least 25 wt %, at least 50 wt %, at least 75 wt %, or at least 90 wt %. In terms of upper limits, the ion exchange resin composition may comprise less than 99 wt % non-metal-functionalized exchange resin, e.g., less than 90 wt %, less than 70 wt %, less than 50 wt %, less than 25 wt %, less than 10 wt %, or less than 1 wt %, while appreciating that some amount of non-metal-functionalized exchange resin should be present in the ion exchange resin composition. In a preferred embodiment, the ion exchange resin comprises approximately 50 wt % metal-functionalized exchange resin and approximately 50 wt % non-metal-functionalized exchange resin. In anther embodiment, the ion exchange resin comprises approximately 75 wt % metal-functionalized exchange resin and approximately 25 wt % non-metal-functionalized exchange resin. Some exemplary ion exchange resin compositions are provided in Table 2.

TABLE 2

Exemplary Ion Exchange Resin Compositions

| Component | Wt % Range | Wt % Range | Wt % Range |
|---|---|---|---|
| Metal-Functionalized Resin | 1 to 99 | 10 to 90 | 25 to 75 |
| Non-Metal Functionalized Resin | 1 to 99 | 10 to 90 | 25 to 75 |

The ion exchange resin composition, in some embodiments may have an overall metal content of at least 1 wt % metal, e.g., at least 10 wt % or at least 25 wt %. In terms of upper limits, the ion exchange resin composition may have an overall metal content less than 35 wt % metal, e.g., less than 25 wt % or less than 10 wt %.

The metal of the metal-functionalized exchange resin may vary widely as is known in the art. In one embodiment, the metal-functionalized exchange resin is functionalized with a metal selected from the group consisting of silver, mercury, palladium, and rhodium. Preferably, the functionalizing metal comprises silver. Preferred resin/metal combinations include styrene/divinyl benzene polymer, e.g., Amberlyst™ 15, functionalized with silver.

Use of the Ion Exchange Resin Composition

Carboxylic acid streams, e.g., acetic acid streams, that are contaminated with a halides and/or corrosion metals may be contacted with the inventive ion exchange resin composition under a wide range of operating conditions. Preferably, the ion exchange resin composition is provided in a guard bed. The use of guard beds to purify contaminated carboxylic acid streams is well documented in the art (see, for example, U.S. Pat. Nos. 4,615,806; 5,653,853; 5,731,252; and 6,225,498, which are hereby incorporated by reference in their entireties). Generally, a contaminated liquid carboxylic acid stream is contacted with the inventive ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

Similar iodide contamination issues may exist in acetic anhydride manufactured via a rhodium-iodide catalyst system. Thus, the inventive ion exchange resins, guard beds, and processes may alternatively be utilized in the purification of crude acetic anhydride product streams.

The pressure during the contacting step is limited only by the physical strength of the resin. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at about atmospheric pressure, which is generally preferred based on economic considerations, the temperature may range from 17° C. (the freezing point of acetic acid) and about 118° C. (the boiling point of acetic acid). It is within the purview of those skilled in the art to determine analogous ranges for product streams comprising other carboxylic acid compounds. The temperature of the contacting step preferably is kept relatively low to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin degrading (via the mechanism of acid-catalyzed aromatic desulfonation) at temperatures of about 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for halide removal.

The configuration of the guard bed within an acetic acid purification train may vary widely. For example, the guard bed may be configured after a final drying column. Additionally or alternatively, the guard be may be configured after a final heavy ends removal column. Preferably the guard bed is configured in a position wherein the temperature acetic acid product stream is low, e.g., less than 120° C. or less than 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In one embodiment, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

A purified acetic acid composition is obtained as a result of the guard bed treatment. The purified acetic acid composition, in one embodiment, comprises less than 100 wppb, iodides, e.g., less than 90 wppb, less than 50 wppb, or less than 25 wppb. In one embodiment, the purified acetic acid composition comprises less than 100 wppb corrosion metals, e.g., less than 750 wppb, less than 500 wppb, or less than 250 wppb. In terms of ranges, the purified acetic acid composition may comprise from 0 to 100 wppb iodides, e.g., from 1 to 50 wppb; and/or from 0 to 1000 wppb corrosion metals, e.g., from 1 to 500 wppb. In other embodiments, the guard bed removes at least 25 wt % of the iodides from the crude acetic acid product, e.g., at least 50 wt % or at least 75 wt %. In one embodiment, the guard bed removes at least 25 wt % of the corrosion metals from the crude acetic acid product, e.g., at least 50 wt % or at least 75 wt %.

Production of the Ion Exchange Resin Composition

Processes for functionalizing exchange resins are well known (see, for example, U.S. Pat. Nos. 4,615,806; 5,139,981; and 5,227,524, which are hereby incorporated by reference in their entireties). The preparation of the metal-functionalized exchange resin component of the inventive ion exchange resin composition may be achieved by any of the methods known in the art. For example, a metal salt, e.g., a silver or palladium salt, having a reasonable solubility in water or a suitable non-aqueous organic medium can be used in the functionalizing step. Silver acetate and silver nitrate are exemplary salts that may used for functionalizing the resin. In a case where mercury is desired, a suitable salt may be mercuric acetate. The organic medium that may be used to load silver ions on the exchange resin may be, for example, acetic acid.

In one embodiment, an ion exchange resin may be converted to the metal salt, e.g., metal-functionalized form, by contacting the exchange resin with a solution of the desired silver or mercury salt, for a sufficient length of time to allow for association of the metal ions with the resin. As some metal may be leached from the metal-functionalized ion exchange resin during conditions of actual use, it may be useful to have a bed of ion-exchange resin which has not been previously functionalized, placed downstream of the bed of metal-functionalized ion exchange resin.

When preparing the metal-functionalized exchanged resin, commercially available cation exchange resins should be pre-washed with distilled water to remote any water-soluble acidic material and reducing substances. This acidic material renders inaccurate the indirect measurement of exchange through measurement of the increase in acidity as silver replaces hydrogen ions on the resin. Also, reducing agents lead to the formation of colloidal silver, which remains in the water-acid mixture rather than bonding to the resin. This colloidal silver represents a small economic loss and is difficult to remove. Distilled water may be used to avoid introduction of undesirable contaminants.

It is within the scope of the present invention to prepare a metal-functionalized gel resin by using gel resin, instead of a macroreticulated resin, as the starting material.

General Carbonylation Processes

The features of the present invention may be applied to any suitable methanol carbonylation process. For example, the formation of acetic acid via a carbon monoxide/methanol carbonylation reaction may be carried out by reacting methanol and/or methanol derivatives with carbon monoxide. Other exemplary carbonylation systems, including reaction zone and separation zones, that may be used with embodiments of the present invention include those described in U.S. Pat. Nos. 7,223,886; 7,202,382; 7,005,541; 6,657,078; 6,339,171; 5,917,089; 5,840,969; 5,731,252; 5,672,743; 5,144,068; 5,026,908; 5,001,259; 4,994,608, 3,769,329; and U.S. Pub. Nos. 2008/0287706, 2008/0293966, 2009/0107833, 2009/0270651. An additional methanol carbonylation process is disclosed in U.S. patent application Ser. No. 12/892,348. These documents are hereby incorporated by reference in their entireties. Commercial examples of these carbonylation processes include the Monsanto process and the Cativa™ process. In a preferred embodiment, the crude acetic acid product to be purified is produced via a low water carbonylation method, e.g., one in which the concentration of water maintained in a liquid reaction composition is less than 14 wt %, e.g., less than 10 wt % or less than 7 wt %. In another embodiment, the concentration of water maintained in a liquid reaction composition ranges from 0.1 wt. % to 14 wt. %.

EXAMPLES

The following non-limiting examples are provided to better illustrate embodiments of the present invention.

Example 1

A silver-functionalized resin was prepared in accordance with the present invention. To prepare the silver-functionalized resin component, a stock solution of silver acetate was prepared. A known quantity of resin was mixed with the silver acetate in a 50/50 acetic acid/water solution to achieve a silver loading of approximately 20% in the silver-functionalized component. These mixtures were then shaken for 24 hours to achieve sufficient uptake of the silver by the sulfonic acid resin. The silver-functionalized resin component was then combined with non-metal-functionalized resin, i.e., no silver loading, to achieve the desired exchange resin composition having an overall silver loading of approximately 10%.

Comparative Example A

To prepare the silver-functionalized resin, a stock solution of silver acetate was prepared. A known quantity of resin was mixed with the silver acetate in a 50/50 acetic acid/water solution to achieve a silver loading of approximately 10% in the silver-functionalized component. These mixtures were then shaken for 24 hours to achieve sufficient uptake of the silver by the sulfonic acid resin. No non-metal functionalized resin was added to the silver-functionalized resin.

Iodide Removal

Crude acetic acid compositions comprising an acid composition comprising acetic acid, iodides (iodohexane), and optionally corrosion metals were fed to guard beds to remove impurities therefrom. Guard bed 1 was packed with the silver-functionalized resin of Example 1. Guard bed 2 was packed with the silver-functionalized resin of Comparative Example A. The results of the iodide removal are shown in Table 3.

TABLE 3

| Iodide Removal from Crude Acetic Acid Stream | | |
|---|---|---|
| Time, hours | Guard Bed 1<br>% $C_6$ Iodide<br>Removed | Guard Bed 2<br>% $C_6$ Iodide<br>Removed |
| 1 | 99.7 | 99.5 |
| 3 | 71.8 | 75.5 |
| 5 | 42.4 | 48.6 |
| 7 | 16.4 | 12.7 |
| 9 | 9.9 | 7.0 |
| 11 | 5.3 | 3.3 |
| 13 | 0.5 | 1.5 |
| 15 | 0.0 | 0.3 |

As shown in Table 3, the exchange resin composition of Example 1 and the exchange resin of Comparative Example A removed similar amounts of iodide from the respective crude acetic acid composition. Each of these exchange resin composition had similar overall silver loading percentages. The exchange resin of Example 1, however, required a significantly smaller quantity of silver-functionalized resin, e.g., half as much as Comparative Example A.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all hereby incorporated by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. An ion exchange resin composition comprising:
a mixture comprising:
(a) a metal ion-functionalized exchange resin comprising from 3% to 94% metal ion-functionalized active sites; and
(b) a non-metal ion-functionalized exchange resin comprising non-metal ion-functionalized active sites, wherein the percentages are based on the total number of sites of the metal ion-functionalized exchange resin and the non-metal ion-functionalized exchange resin;
wherein the non-metal ion-functionalized exchange resin does not contain any metal ion-functionalized active sites; and
wherein the non-metal ion-functionalized exchanged resin optionally comprises non-metal ion-functionalization.

2. The ion exchange resin composition of claim 1, wherein the amounts of (a) and (b) correspond, within a ±25% margin of error, to an iodide content and a corrosion metal content, respectively, in a crude acetic acid composition.

3. The ion exchange resin composition of claim 1, wherein the amounts of (a) and (b) correspond, within a ±10% margin of error, to an iodide content and a corrosion metal content, respectively, in a crude acetic acid composition.

4. The ion exchange resin composition of claim 1, wherein the ratio of metal ion-functionalized active sites to non-metal ion-functionalized active sites corresponds to a molar ratio of iodides to corrosion metals in a crude acetic acid composition.

5. The ion exchange resin composition of claim 1, wherein the ratio of non-metal ion-functionalized active sites to metal ion-functionalized active sites ranges from 1:0.05 to 1:35.

6. The ion exchange resin composition of claim 1, wherein the ion exchange resin composition comprises at least 3% metal ion-functionalized active sites, and at least 3% non-metal ion-functionalized active sites, wherein the percentages are based on the total number of sites of the metal ion-functionalized exchange resin and the non-metal ion-functionalized exchange resin.

7. The ion exchange resin composition of claim 1, wherein the ion exchange resin composition comprises at least 10% metal ion-functionalized active sites, and at least 10% non-metal ion-functionalized active sites, wherein the percentages are based on the total number of sites of the metal ion-functionalized exchange resin and the non-metal ion-functionalized exchange resin.

8. The ion exchange resin composition of claim 1, wherein the ion exchange resin composition comprises:
from 1 wt. % to 99 wt. % metal ion-functionalized exchange resin; and
from 1 wt. % to 99 wt. % non-metal ion-functionalized exchange resin, wherein the percentages are based on the total weight of the metal ion-functionalized exchange resin and the non-metal ion-functionalized exchange resin.

9. The ion exchange resin composition of claim 1, wherein the ion exchange resin composition comprises:
from 10 wt. % to 90 wt. % metal ion-functionalized exchange resin; and
from 10 wt. % to 90 wt. % non-metal ion-functionalized exchange resin, wherein the percentages are based on the total weight of the metal ion-functionalized exchange resin and the non-metal ion-functionalized exchange resin.

10. The ion exchange resin composition of claim 1, wherein the ion exchange resin composition comprises:
from 25 wt. % to 75 wt. % metal ion-functionalized exchange resin; and
from 25 wt. % to 75 wt. % non-metal ion-functionalized exchange resin, wherein the percentages are based on the total weight of the metal ion-functionalized exchange resin and the non-metal ion-functionalized exchange resin.

11. The ion exchange resin composition of claim 1, wherein the ion exchange resin composition has a metal content ranging from 1 wt. % to 35 wt. %.

12. The ion exchange resin composition of claim 1, wherein the metal ion-functionalized exchange resin is functionalized with a metal selected from the group consisting of mercury, palladium, and rhodium.

13. The ion exchange resin composition of claim 1, wherein the metal ion-functionalized exchange resin is functionalized with silver ion.

14. The ion exchange resin composition of claim 1, wherein the ion exchange resin composition comprises a base resin selected from the group consisting of polystyrene, styrene/divinyl benzene polymer, polyvinyl pyrrolidone, polyvinyl pyridine, and macroreticulated strong acid cation exchange resins.

15. The ion exchange resin composition of claim 1, wherein the ion exchange resin composition comprises a base resin comprising styrene/divinyl benzene polymer, and wherein the metal ion-functionalized exchange resin is functionalized with silver ion.

16. The ion exchange resin composition of claim 1, wherein the metal ion-functionalized exchange resin comprises a first base resin and the non-metal ion-functionalized exchange resin comprises a second base resin, different from the first base resin.

17. The ion exchange resin composition of claim 1, wherein the metal ion-functionalized exchange resin comprises a first base resin and the non-metal ion-functionalized exchange resin comprises a second base resin, and wherein the first and second base resins are the same material.

18. The composition of claim 1, wherein:
the non-metal ion-functionalized exchange resin comprises discrete particles, each particle comprising no metal ion-functionalized sites.

19. The composition of claim 18, wherein:
the metal ion-functionalized exchange resin comprises discrete particles, each particle comprises metal ion-functionalized sites.

* * * * *